(12) United States Patent
Hu et al.

(10) Patent No.: US 10,098,966 B2
(45) Date of Patent: Oct. 16, 2018

(54) COMPLEX PARTICLES FOR DELIVERING NITRIC OXIDE, METHOD OF PRODUCING THE SAME, AND APPLICATION OF THE SAME

(71) Applicant: National Defense Medical Center, Taipei (TW)

(72) Inventors: Teh-Min Hu, New Taipei (TW); Dueng-Yuan Hueng, Taipei (TW); Jen-Kun Chen, Hsinchu (TW); Hsin-Ying Clair Chiou, New Taipei (TW); Li-Hui Tsai, New Taipei (TW)

(73) Assignee: NATIONAL DEFENSE MEDICAL CENTER, Taipei (TW)

( * ) Notice: Subject to any disclaimer, the term of this patent is extended or adjusted under 35 U.S.C. 154(b) by 0 days.

(21) Appl. No.: 15/640,529

(22) Filed: Jul. 1, 2017

(65) Prior Publication Data

US 2018/0000955 A1    Jan. 4, 2018

Related U.S. Application Data

(60) Provisional application No. 62/357,422, filed on Jul. 1, 2016.

(51) Int. Cl.
| | | |
|---|---|---|
| *A61K 9/00* | (2006.01) | |
| *A61K 47/59* | (2017.01) | |
| *A61K 33/00* | (2006.01) | |
| *A61K 47/69* | (2017.01) | |
| *A61K 31/495* | (2006.01) | |
| *A61K 9/50* | (2006.01) | |
| *C08K 5/548* | (2006.01) | |
| *A61K 9/51* | (2006.01) | |

(52) U.S. Cl.
CPC .......... *A61K 47/593* (2017.08); *A61K 9/0085* (2013.01); *A61K 9/5031* (2013.01); *A61K 9/5153* (2013.01); *A61K 31/495* (2013.01); *A61K 33/00* (2013.01); *A61K 47/6941* (2017.08); *C08K 5/548* (2013.01)

(58) Field of Classification Search
CPC .................................................. A61K 47/593
See application file for complete search history.

(56) References Cited

PUBLICATIONS

Chou, Direct Formation of S-Nitroso Silica Nanoparticles from a Single Silica Source, Langmuir, 2014, 30(3), 812-822.*

* cited by examiner

*Primary Examiner* — Paul W Dickinson
(74) *Attorney, Agent, or Firm* — Locke Lord LLP; Tim Tingkang Xia, Esq.

(57) ABSTRACT

The present invention relates to complex particles for delivering nitric oxide, method of producing the particles, and application of the particles, and more particularly, relates to complex particles for delivering nitric oxide and an additional therapeutic reagent.

19 Claims, 18 Drawing Sheets

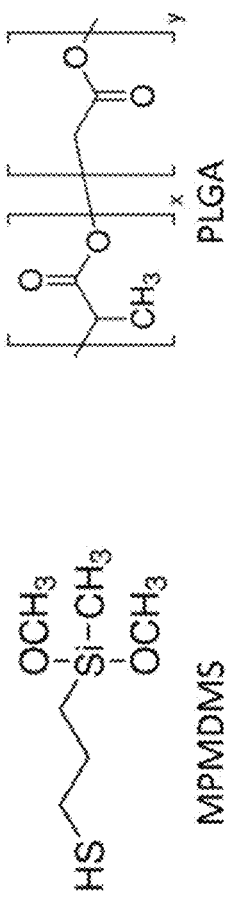
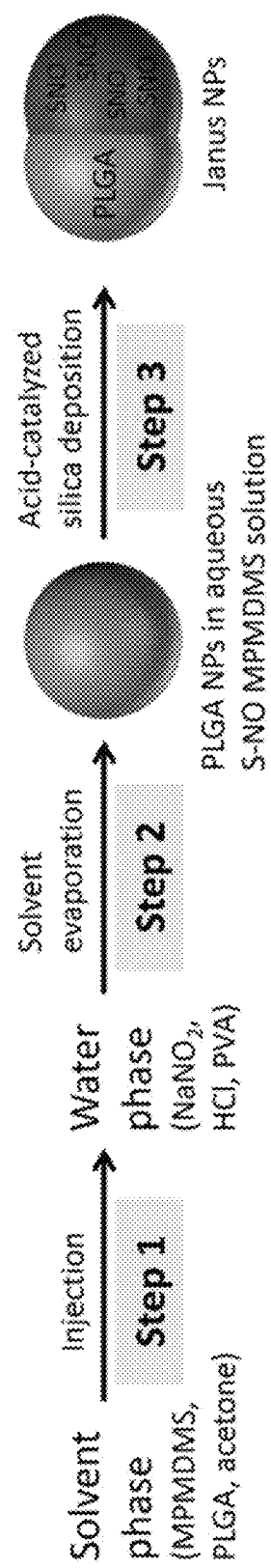
Figure 1A
Figure 1B
Figure 1C

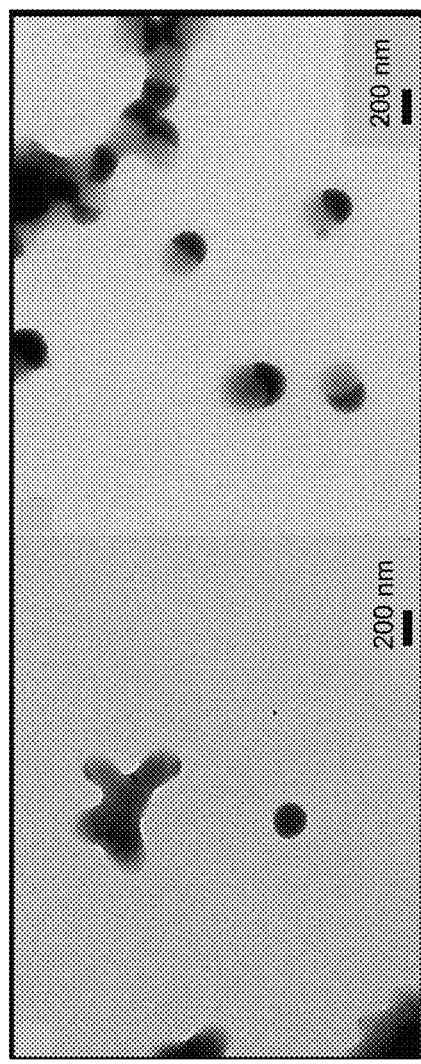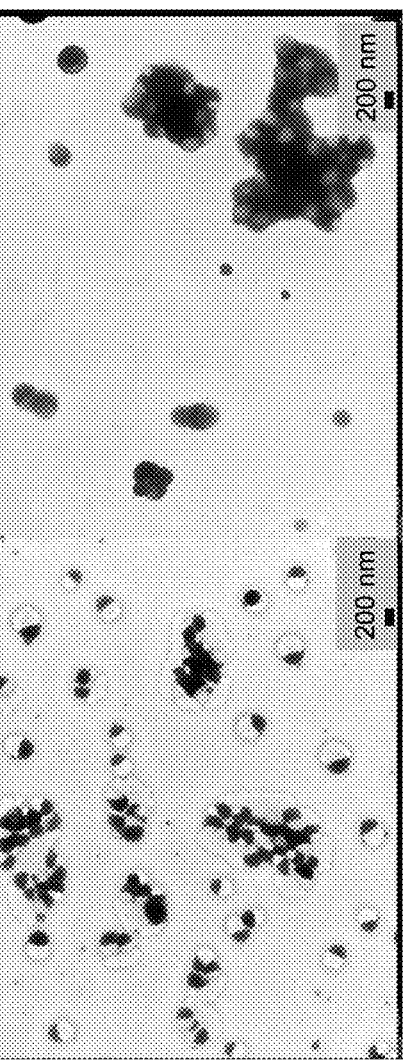

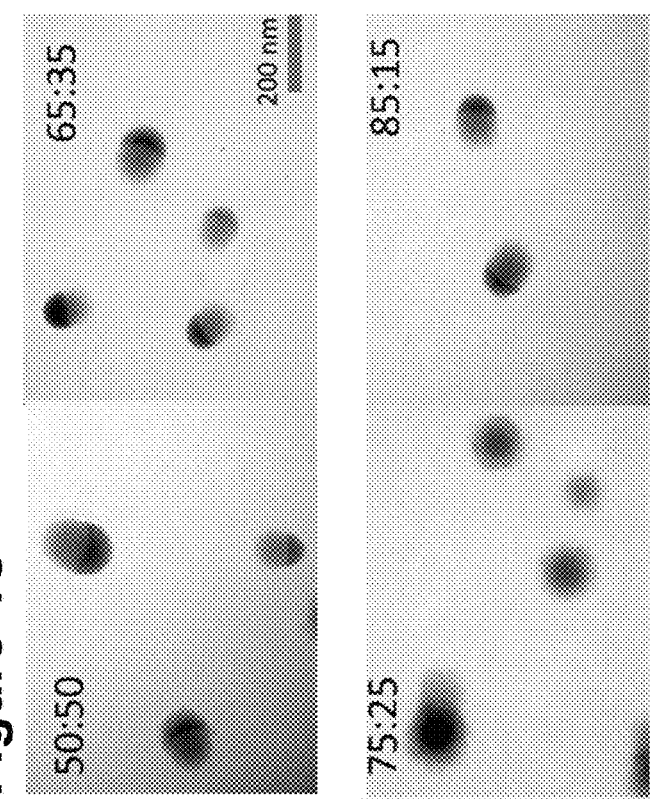
*Figure 4C*
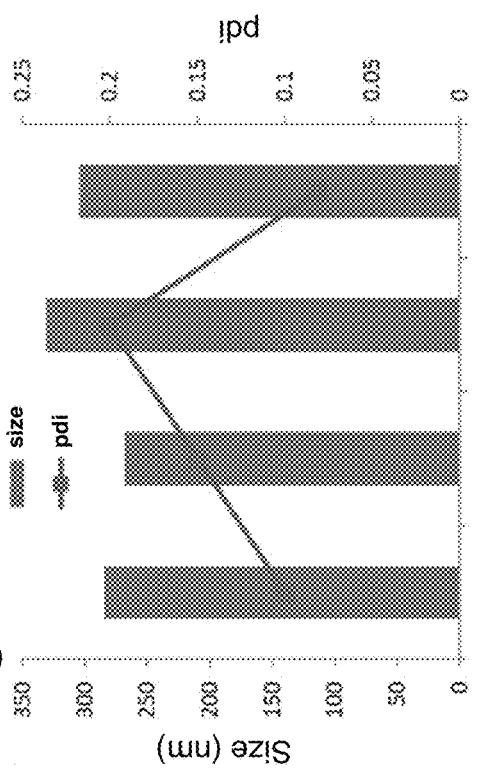
*Figure 4A*
| PLGA type (L:G ratio) | MW | NO content (mM) |
|---|---|---|
| 50:50 | [η] = 0.33 dl/g | 11.4 |
| 65:35 | 40000-75000 | 5.69 |
| 75:25 | 66000-107000 | 7.23 |
| 85:15 | 50000-75000 | 5.12 |
*Figure 4B*

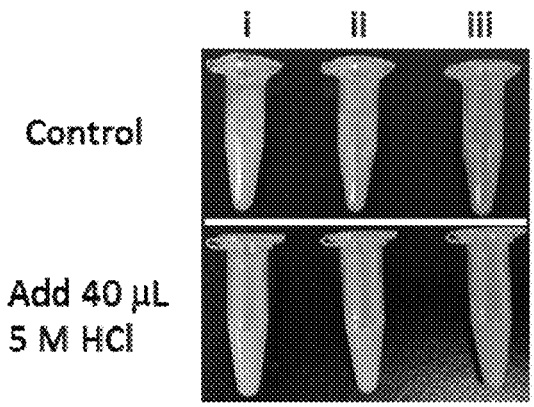
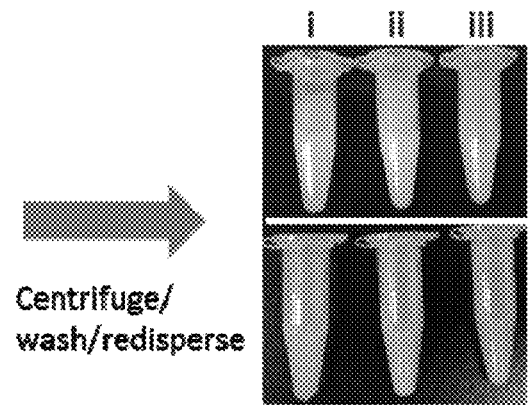
Figure 5A  Figure 5B
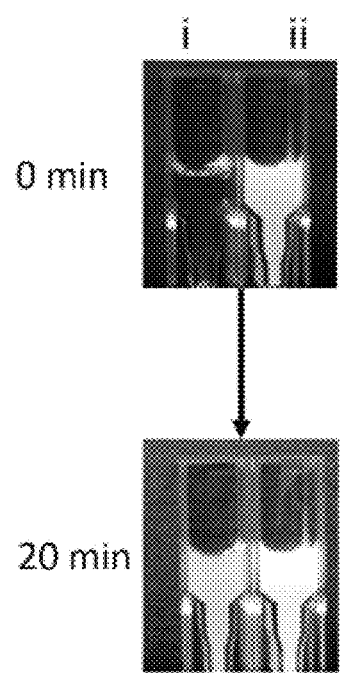
i. without PLGA NPs
ii. with PLGA NPs
Figure 6A

COMPLEX PARTICLES FOR DELIVERING NITRIC OXIDE, METHOD OF PRODUCING THE SAME, AND APPLICATION OF THE SAME

CROSS-REFERENCE TO RELATED APPLICATION

This application claims priority to and the benefit of, pursuant to 35 U.S.C. § 119(e), U.S. provisional patent application Ser. No. 62/357,422, filed Jul. 1, 2016. The entire contents of the above identified applications are incorporated herein by reference.

Some references, if any, which may include patents, patent applications and various publications, may be cited and discussed in the description of this invention. The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD

The present invention relates to complex particles for delivering nitric oxide, method of producing the particles, and application of the particles, and more particularly, relates to complex particles for delivering nitric oxide and an additional therapeutic reagent.

BACKGROUND

In the field of drug delivery science, there is a recent trend in developing nanoparticle (NP) formulations that can simultaneously deliver two or more drugs with different therapeutic targets (i.e. co-delivery). Although such an approach in pharmaceutical drug development is scientifically attractive, the concept remains to be technically challenging. First, the loaded drugs often have distinct physicochemical properties (e.g. hydrophobic vs. hydrophilic); therefore, it is difficult, if not impossible, to achieve the same loading efficiency within a polymeric carrier material. Second, to achieve effective combination therapy, it is desirable to tune the release profiles of the co-loaded drugs, so that one drug may release faster and the other slower. However, within the same nanostructure, this cannot be easily achieved. Third, potential chemical interaction should be considered when two drugs are co-existing within the same nanoparticle confinement.

SUMMARY

In one aspect, the present invention relates to complex particles for delivering nitric oxide. The complex particle for delivering nitric oxide comprises a poly(Lactide-co-Glycolide) (PLGA) nanoparticle and a S-nitroso-silica species depositing on the PLGA nanoparticle.

In some embodiments, the complex particle is made by the steps of: injecting an organic phase to a water phase to obtain a mixture, the organic phase containing (3-Mercaptopropyl)methyldimethoxysilane (MPMDMS) and PLGA in acetone, and the water phase containing poly(vinyl alcohol) (PVA), sodium nitrite, and hydrochloric acid (HCl) in water; removing acetone from the mixture; and adding a second HCl to the mixture to initiate silica disposition.

In some preferable embodiments, the PLGA has a lactide/glytide ratio, and the lactide/glytide ratio is 50/50 to 85/15. In some preferable embodiments, the MPMDMS has a concentration ranging from 20 to 80 mM.

In some preferable embodiments, the complex particle further comprises a drug loaded on the PLGA nanoparticle. In some preferable embodiments, the complex particle further comprising a drug loaded on the PLGA nanoparticle is made by the steps of: injecting an organic phase to a water phase to obtain a mixture, the organic phase containing MPMDMS, PLGA, and a drug in acetone, and the water phase containing PVA, sodium nitrite, and HCl in water; removing acetone from the mixture; and adding a second HCl to the mixture to initiate silica disposition. In some preferable embodiments, the PLGA has a lactide/glytide ratio, and the lactide/glytide ratio is 50/50 to 85/15. In some preferable embodiments, the MPMDMS has a concentration ranging from 20 to 80 mM.

In another aspect, the present invention relates to a method of producing the complex particles for delivering nitric oxide. The method comprises the steps of: injecting an organic phase to a water phase to obtain a mixture, the organic phase containing MPMDMS and PLGA in acetone, and the water phase containing PVA, sodium nitrite, and HCl in water; removing acetone from the mixture; and adding a second HCl to the mixture to initiate silica disposition.

In some preferable embodiments, the PLGA has a lactide/glytide ratio, and the lactide/glytide ratio is 50/50 to 85/15. In some preferable embodiments, the MPMDMS has a concentration ranging from 20 to 80 mM.

In some preferable embodiments, the organic phase further contains a drug in acetone.

In yet another aspect, the present invention relates to application of the complex particles for delivering nitric oxide. The present invention provides a method for inhibiting tumor growth, comprising administering an effective amount of the complex particle for delivering nitric oxide of the present invention to a subject in need.

In some preferable embodiments, the complex particle of the present invention is made by the steps of: injecting an organic phase to a water phase to obtain a mixture, the organic phase containing MPMDMS and PLGA in acetone, and the water phase containing PVA, sodium nitrite, and HCl in water; removing acetone from the mixture; and adding a second HCl to the mixture to initiate silica disposition.

In some preferable embodiments, the PLGA has a lactide/glytide ratio, the lactide/glytide ratio is 50/50 to 85/15, and the MPMDMS has a concentration ranging from 20 to 80 mM.

In some preferable embodiments, the complex particle of the present invention further comprises an anti-cancer drug loaded on the PLGA nanoparticle. The complex particle comprising an anti-cancer drug loaded on the PLGA nanoparticle is made by the steps of: injecting an organic phase to a water phase to obtain a mixture, the organic phase containing MPMDMS, PLGA, and the anti-cancer drug in acetone, and the water phase containing PVA, sodium nitrite, and HCl in water; removing acetone from the mixture; and adding a second HCl to the mixture to initiate silica disposition. In some preferable embodiments, the PLGA has a lactide/glytide ratio, the lactide/glytide ratio is 50/50 to 85/15, and the MPMDMS has a concentration ranging from 20 to 80 mM.

These and other aspects will become apparent from the following description of the preferred embodiment taken in conjunction with the following drawings.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 1A shows the structure of MPMDMS of the Janus PLGA-silica nanoparticles.

FIG. 1B shows the structure of PLGA of the Janus PLGA-silica nanoparticles.

FIG. 1C shows preparation procedures (C) of the Janus PLGA-silica nanoparticles.

FIG. 2A shows the TEM image of Control particles, MPMDMS was at the concentration of 20 mM.

FIG. 2B shows the TEM image of Janus particles formed at the condition of 20 mM MPMDMS.

FIG. 2C shows the TEM image of Janus particles formed at the condition of 40 mM MPMDMS.

FIG. 2D shows the TEM image of Janus particles formed at the condition of 80 mM MPMDMS.

FIG. 4A shows hydrodynamic particle sizes and polydispersity (pdi) of Janus nanoparticles prepared using PLGA with different lactide/glycolide ratio.

FIG. 4B shows NO content of Janus nanoparticles prepared using PLGA with different lactide/glycolide ratio.

FIG. 4C shows TEM images of Janus nanoparticles prepared using PLGA with different lactide/glycolide ratio.

FIG. 5A shows the appearance of reaction solution before the purification step at various MPMDMS concentrations (i) 20 mM, (ii) 40 mM, and (iii) 80 mM.

FIG. 5B shows the appearance of the reaction solution after the purification step at various MPMDMS concentrations (i) 20 mM, (ii) 40 mM, and (iii) 80 mM.

FIG. 6A shows the images taken at the initial time and 20 min after adding 40 μL of HCl (5 M) to initiate silica deposition for SNO-silica formation and deposition with and without PLGA NPs.

DETAILED DESCRIPTION

Figure 3:
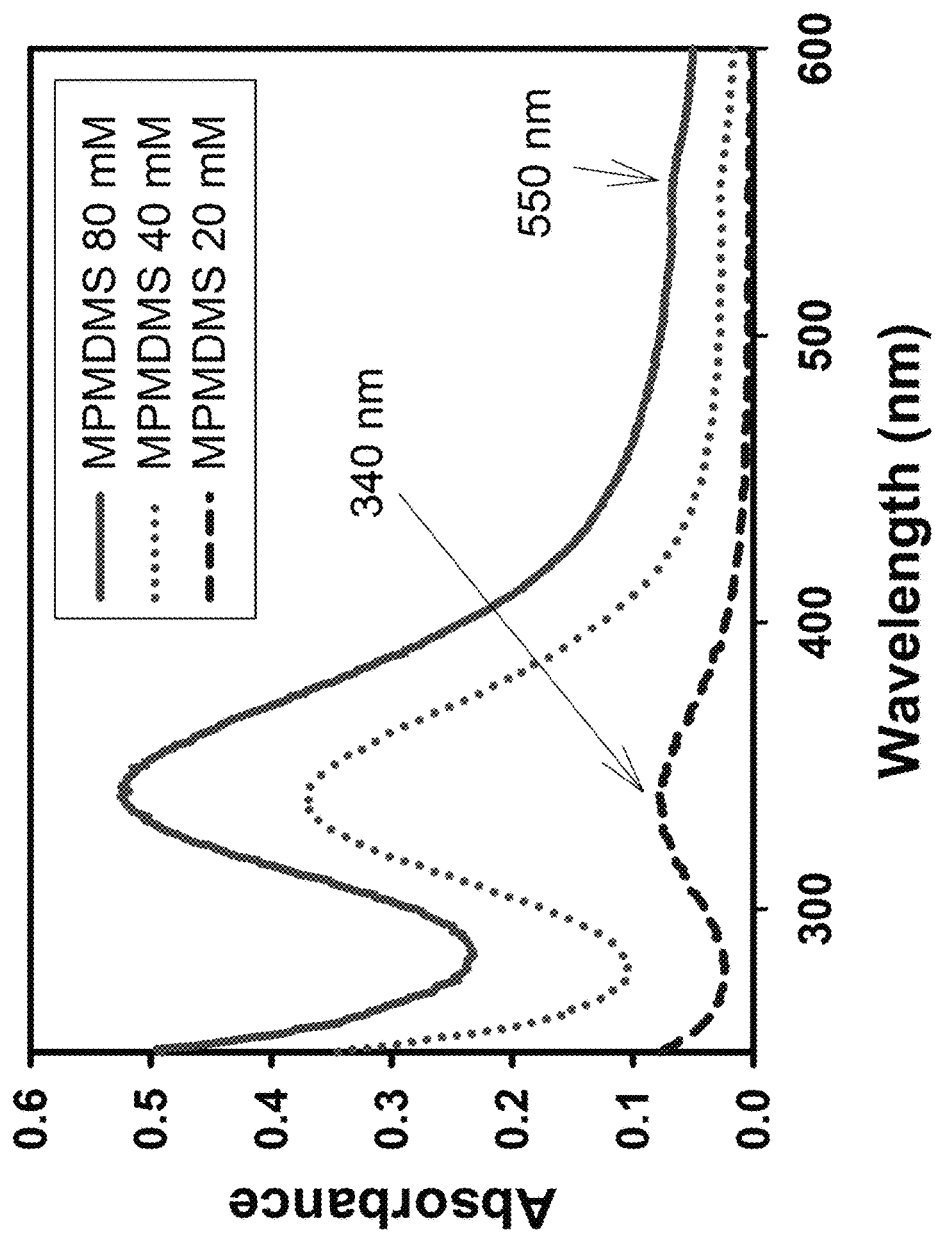
FIG. 3 shows the UV-visible absorption spectra of nanoparticle dispersion prepared at different MPMDMS concentrations (final concentrations in the acetone-water mixture).

Nitric oxide (NO) is an extremely unstable radical molecule with multiple physiological and pathophysiological functions. Given the drawbacks of small-molecular NO donors (a small molecule that release NO), NO-releasing nanoformulations have been studied for achieving sustained and targeted delivery of NO. The various nanoformulations of NO have been implicated in antibiotic and anticancer therapies (Carpenter et al., Influence of scaffold size on bactericidal activity of nitric oxide-releasing silica nanoparticles. *ACS Nano* 2011, 5, (9), 7235-44.). Co-delivery of NO and traditional therapeutic agents is a system in which NO-donating moiety and the co-loaded drug are embedded in the same nanoparticle compartment. To reduce potential NO-drug interaction within the nanostructure, the concept of Janus particles is employed in the present invention. Specifically, the NO-donating component may have a minimized interaction with the other drug if the two entities are physically separated in a Janus particle. Thus, it would represent a breakthrough if the synthesis of NO-donating component can be directed so that it mainly accumulates on one side of a nanoparticle. Herein, the present invention provides a facile method to directly synthesize a PLGA-silica Janus nanoparticles with a distinct NO-releasing silica domain.

As used herein, the term "Janus nanoparticles" refers to particles with a binary two-face feature. Two different reagents with different characteristics (such as high water solubility and low water solubility) can be simultaneously loaded in Janus nanoparticles with two-phases (polymer-lipid).

As used herein, the term "complex particle" refers to a particle having at least two different characteristics, such as a binary two-face feature. An example of a complex particle is a Janus nanoparticles.

As used herein, the term "an effective amount" refers to an amount of the complex particle for delivering nitric oxide of the present invention which is sufficient to delay the onset of an uncontrollable growth of abnormal cells, to decrease the growth rate of cancer cells, to inhibit tumor growth, or to provide any therapeutic benefit in the treatment or management of a disease, especially a cancer.

As used herein, the term "an anti-cancer drug" refers to effective materials that can delay the onset of an uncontrollable growth of abnormal cells, decrease the growth rate of cancer cells, inhibit tumor growth, or kill cancer cells.

As used herein, the singular forms "a", "an", and "the" include plural referents unless the context clearly dictates otherwise. Thus, for example, reference to "a component" includes a plurality of such components and equivalents thereof known to those skilled in the art.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The meaning of the technical and scientific terms as described herein can be clearly understood by a person of ordinary skill in the art.

The present invention is described in more detail in the following illustrative examples. Although the examples may represent only selected embodiments of the invention, it should be understood that the following examples are illustrative and not limiting.

EXAMPLES

Materials and Methods
Reagents
MPMDMS ((3-Mercaptopropyl)methyldimethoxysilane), PLGA (Poly(Lactide-co-Glycolide)), and PVA (Poly(vinyl alcohol)) were purchased from Sigma-Aldrich (St. Louis, Mo., U.S.A.). Sodium nitrite (NaNO2) was obtained from J. T. Baker (Phillipsburg, N.J., U.S.A.). Hydrochloric acid was purchased from Merck (Darmstadt, Germany). All chemicals and solvents were of reagent grade and used as received. Deionized water (18.2 MΩ·cm at 25° C., Millipore Milli-Q) was used throughout the examples.

Preparation of Janus PLGA-Silica Nanoparticles

FIG. 1C depicts a three-step procedure for synthesis of S-nitroso (SNO) carrying PLGA-silica Janus nanoparticles. In the first step, MPMDMS (typically 100 µmol) (FIG. 1A) and PLGA (20 mg) (FIG. 1B) was dissolved in 2 mL of acetone and then injected to 3 mL of water containing PVA (0.5%), sodium nitrite (100 µmol) and HCl (0.033 M). In this step, MPMDMS was used as the single silane source in which a mercaptopropyl group is attached to methyl dimethoxysilane. The thiol group in MPMDMS can be easily modified via S-nitrosation to form S-nitrosothiol linkage for NO storage and release. To initiate the synthesis, the silane source and PLGA were first dissolved in acetone (the solvent phase). The first step involves a rapid injection of the solvent phase to an acidified water phase containing sodium nitrite, HCl and PVA in water. Upon injection, PLGA nanoparticles (NPs) were instantaneously formed through solvent displacement (i.e. nanoprecipitation). Besides that, S-nitrosation occurred immediately after mixing as the solution became intensely red.

In the second step, the reddish solution was subjected to solvent evaporation to remove acetone. Acetone in the reaction mixture was evaporated using Rotavapor at 30 □C for 30 min. For a 5-mL reaction mixture, the final volume of the resulting aqueous particle dispersion was less than 3 mL, which was brought up to 3 mL by adding an adequate amount of water for obtaining a consistent result.

In the final step, further addition of HCl to the solvent-evaporated solution triggered the deposition of SNO-silica species on PLGA nanoparticles. Forty (40) µL of HCl (5 M) was added to the aqueous particle dispersion to initiate silica deposition. After standing for 30 min, the particle dispersion was centrifuged at 5500 rpm (7591×g) for 30 min at 4° C. to remove unreacted supernatant. The pellet was washed with 20 mL of ice-cold water. Finally, the washed particles were redispersed in 1 mL of deionized water. It should be noted that the preparation should be conducted in a manner that light exposure is limited.

Optimization of the Preparation Condition

Several key preparation parameters were identified and extensively studied for obtaining an optimized result: silane concentrations, the amount of HCl, reaction time, and the type of PLGA. Specifically, the MPMDMS concentrations were varied from 20 to 80 mM. The amount of HCl (5 M) added in the final step was 0, 10, 20, 40, 80 µL. The reaction time was varied from 30 min to 120 min. Moreover, PLGA polymers with various lactide/glytide ratios (L/G ratios; 50/50, 65/35, 75/25, 85/15) were used for preparation.

Mechanistic Studies

Silica deposition was studied in more details based on kinetic measurements. To this end, the aqueous particle dispersion after the second step was centrifuged to separate the PLGA particles from the bulk solution containing SNO-silane species. The resulting transparent supernatant (the "SNO silica soup") was collected for the following experiment.

In the first experiment, silica deposition after adding HCl to the particle-free SNO silica soup was studied. After adding various concentrations of HCl, the formation of silica particles was followed kinetically using turbidity (optical density (OD) at 800 nm) and hydrodynamic size measurements. Moreover, by varying the amount of HCl added, the time courses for SNO decay and turbidity changes in the solution were simultaneously monitored and correlated.

In the second experiment, the particle-free SNO silica soup was replenished with various amounts of polystyrene NPs (100 nm) and upon HCl addition the turbidity change over time was followed. At the end of reaction, particle sizes were determined and the pellet of particles was obtained by centrifugation for direct visual observation of the particle appearance.

Physicochemical Characterization of Janus Particles

Hydrodynamic particle sizes were measured using dynamic-light-scattering (DLS; LB-500, Horiba instruments Inc.). For each sample (1 mL), three readings were taken and the mean value was used. To determine surface charges of Janus particles, a total of 10 zeta-potential readings were recorded and averaged (ZetaPlus, Brookhaven Instruments Co.). The TEM images were taken from Hitachi HT7700. The sample was placed on a carbon-Formvar-coated copper grid (300 mesh, type A; Electron Microscopy Sciences), then air-dried for 3 h before taking the TEM picture. The amounts of SNO groups in the reaction mixture were determined by spectrophotometric measurements at 330 nm.

Kinetics of Nitric Oxide Release

The remaining SNO contents in Janus particles were determined spectrophotometrically. The purified particles were dispersed and diluted in 1 mL of deionized water. At predetermined time intervals, the particle dispersion was measured for optical density (OD) at 330 nm. The remaining SNO amount was calculated as: % SNO remaining=100× $(OD_t-OD_{inf})/(OD_0-OD_{inf})$, where ODt is the absorbance value at 330 nm at time t; $OD_0$ is the initial value, and $OD_{inf}$ is the value measured after completely release of NO (i.e. at the time when the color of particles changed from pink to pale white).

Preparation of Janus PLGA-Silica Nanoparticles for Delivering Nitric Oxide and Temoxolomide (TMZ)

Figure 11:
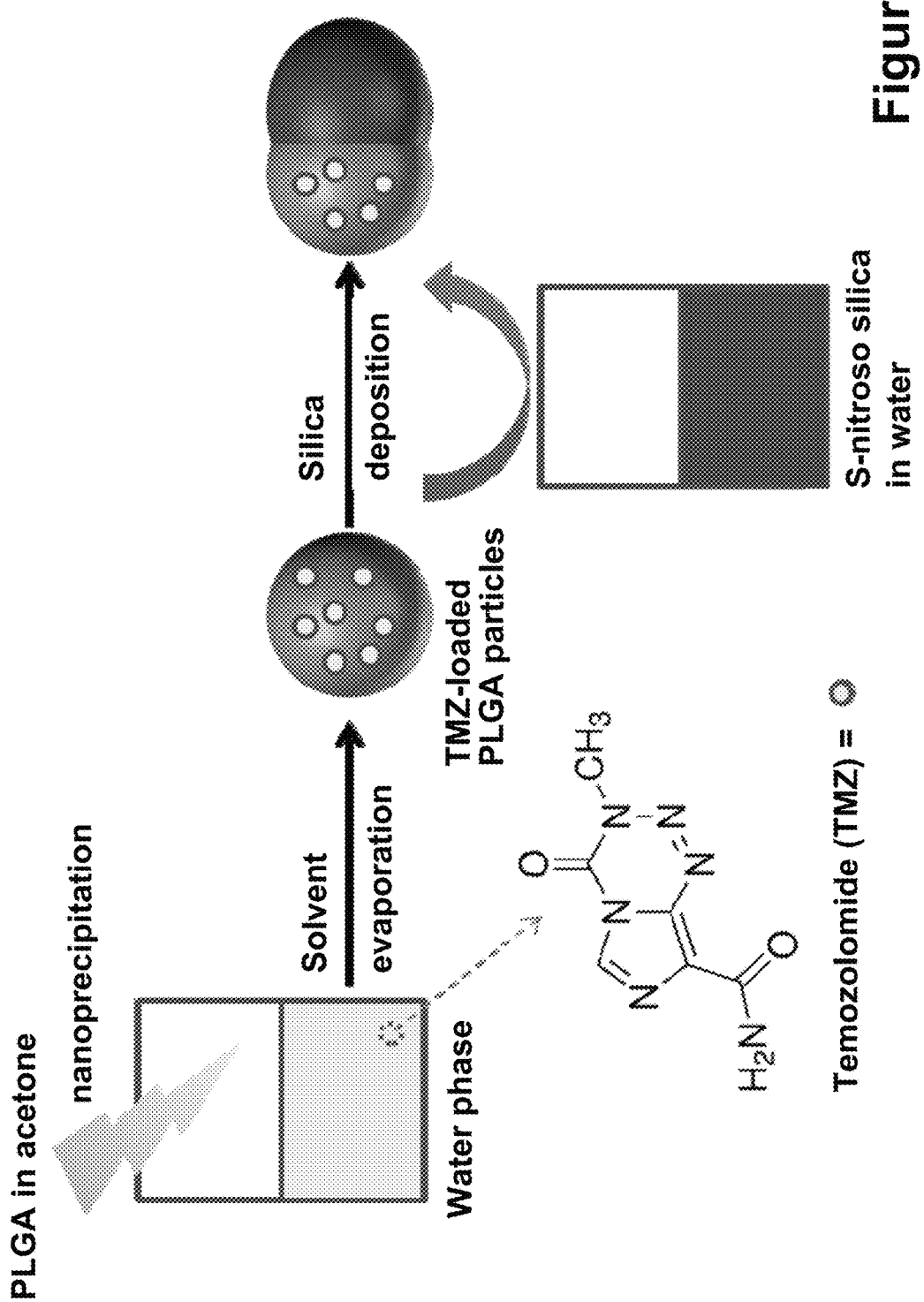
FIG. 11 shows the preparation procedures of the S-nitroso (SNO) carrying TMZ-loaded PLGA-silica Janus nanoparticles.

FIG. 11 depicts a procedure for synthesis of S-nitroso (SNO) carrying TMZ-loaded PLGA-silica Janus nanoparticles. The organic phase consists of 40 mg of PLGA (L/G ratio=50:50; inherent viscosity: 1.32 dL/g) and 2 mg of TMZ dissolved in 2 mL of acetone containing 50 mM of MPM-DMS. The water phase consists of PVA (0.5%), sodium nitrite (33 mM) and HCl (33 mM) in 3 mL of water. Nanoprecipitation was performed by injecting the organic phase (2 mL) to the water phase (3 mL), followed by removing acetone under reduced pressure in a rotary evaporator for 30 min until the final volume was about 3 mL. Then, 120 μL of 5M HCl was added to the resulting solution to initiate silica disposition (avoiding light). After 30 min, the particle dispersion was centrifuged at 4500 rpm (2420 g) for 30 min (4° C.), washed with ice-cold water and resuspended in water. The nitric oxide (NO) content was measured using the Griess assay. The TMZ content was measured using spectrophotometric determination (at 330 nm) of DMSO-extracted particle solution after a complete removal of NO under light irradiation for 2 hr.

Cytotoxicity Assay of Nitric Oxide-Loaded Janus PLGA-Silica Nanoparticles to Cancer Cell Lines Glioblastoma cell lines U87 (ATCC No. HTB-14™), LN229 (CRL-2611™), and GBM8401 (*J Surg Oncol.* 1988; 38(3):173-81) were treated with several concentrations of the Janus PLGA-silica nanoparticles of the present invention to analyze the cytotoxicity of the nanoparticles. Cell viability was determined by MTS assay using the CellTiter 96 Aqueous One Solution Cell Proliferation Assay kit (Promega, Madison, Wis., USA). Cells were plated in 96-well plates (3000 cells/well) with fresh culture medium. Twenty-four hours after plating, cells were treated with various concentrations of NP—NO and incubated for another 72 hours. Subsequently, 20 μl MTS solution was added to each well and incubate for 4 h at 37° C. The same dilution of MTS solution in culture medium alone was used as the background. After incubation, absorbance was recorded at 490 nm. The absorbance optical density (OD) of each well was used to calculate the cell survival rate.

Survival rate $(\%)=[OD_{treated\ cells}-OD_{background}]/OD_{control\ cells}-OD_{background}]\times100\%$.

Furthermore, glioblastoma cell line GBM8401 was treated with 200 μM of Janus PLGA-silica nanoparticles of the present invention for 24 hours. After that, DNA of the cancer cells was labeled with 5-bromo-2'-deoxyuridine (BrdU) with a FITC-BrdU Flow Kit according to the manufacturer's instructions (BD Biosciences), and cell proliferation was analyzed by flow cytometry.

In Vivo Inhibition of Brain Tumor Growth by the Nitric Oxide-Loaded Janus PLGA-Silica Nanoparticles Nude mice bearing brain tumor xenografts were used as the animal model to analyze anticancer effect of the Janus PLGA-silica nanoparticles of the present invention. A human brain malignant glioma cell line, GBM8401-iRL were adjusted to $2.5\times10^4$ cells/μl which suspended in PBS with 50% Matrigel™ Matrix (Corning, Mass., USA). Total of $1\times10^5$ cells (4 μl) were injected into the right cerebral hemisphere of 6-week-old BALB/cAnN.Cg-Foxn1nu/Crl-Narl nude mice using a 10-μl Hamilton syringe with a 26s-gauge needle. The syringe was lowered to a depth of 4 mm. Five days later, the Janus PLGA-silica nanoparticles of the present invention were implanted around the tumors. Seven (7) days after the treatment, sizes of the tumors in the animal model were measured by the In Vivo Imaging System (IVIS). Mice were intraperitoneal injected with 150 mg/kg D-luciferin and the image was acquired. The bioluminescence intensity was quantified based on total flux (photon/sec).

In Vivo Inhibition of Brain Tumor Growth by Combination of the Nitric Oxide-Loaded Janus PLGA-Silica Nanoparticles and TMZ Nude mice bearing brain tumor xenografts were also used as the animal model to analyze anticancer effect of the combination of the Nitric oxide-loaded Janus PLGA-silica nanoparticles of the present invention and a chemotherapy drug TMZ. A human brain malignant glioma cell line, GBM8401-iRL were adjusted to $2.5\times10^4$ cells/μl which suspended in PBS with 50% Matrigel™ Matrix (Corning, Mass., USA). Total of $1\times10^5$ cells (4 μl) were injected into the right cerebral hemisphere of 6-week-old BALB/cAnN.Cg-Foxn1nu/CrlNarl nude mice using a 10-μl Hamilton syringe with a 26s-gauge needle. The syringe was lowered to a depth of 4 mm. Five days later, the Janus PLGA-silica nanoparticles of the present invention were implanted around the tumors, combined with intraperitoneal injection of TMZ for 3 days. Sizes of the tumors in the animal model were traced with the In Vivo Imaging System (IVIS). Mice were intraperitoneal injected with 150 mg/kg D-luciferin and the image was acquired. The bioluminescence intensity was quantified based on total flux (photon/sec).

Cytotoxicity Assay of Nitric Oxide and TMZ-Loaded Janus PLGA-Silica Nanoparticles to Cancer Cell Lines Glioblastoma cell lines LN229 (CRL-2611™) and GBM8401 (*J Surg Oncol.* 1988; 38(3): 173-81) were treated with the Nitric oxide and TMZ-loaded Janus PLGA-silica nanoparticles of the present invention to analyze the cytotoxicity of the nanoparticles. Cell viability was determined by MTS assay using the CellTiter 96 Aqueous One Solution Cell Proliferation Assay kit (Promega, Madison, Wis., USA). Cells were plated in 96-well plates (3000 cells/well) with fresh culture medium. Twenty-four hours after plating, cells were treated with the Janus PLGA-silica nanoparticles loaded both TMZ and various concentrations of nitric oxide and incubated for another 72 hours. Subsequently, 20 µl MTS solution was added to each well and incubate for 4 h at 37° C. The same dilution of MTS solution in culture medium alone was used as the background. After incubation, absorbance was recorded at 490 nm. The absorbance optical density (OD) of each well was used to calculate the cell survival rate.

$$\text{Survival rate } (\%) = [OD_{treated\ cells} - OD_{background}] / OD_{control\ cells} - OD_{background}] \times 100\%.$$

Results
Optimized Condition for Preparation of Janus PLGA-Silica Nanoparticles

The Janus structure was confirmed by TEM (FIG. 2). It can be seen that Janus particles were formed at various MPMDMS concentrations (TEM images, FIGS. 2B-2D). As shown in FIG. 3, the UV-visible spectra of the particle exhibited characteristic absorption wavelengths at 340 and 550 nm of S-nitrosothiols, indicating successful incorporation of SNO species. Moreover, the efficiency of SNO attachment increased when MPMDMS concentration was increased. To demonstrate the versatility of the method, the inventors conducted further synthesis using PLGA with different L/G ratios. The result shows that all produced Janus nanoparticles with SNO loading (FIG. 4).

Formation Mechanism of Janus PLGA-Silica Nanoparticles

Figure 6B:
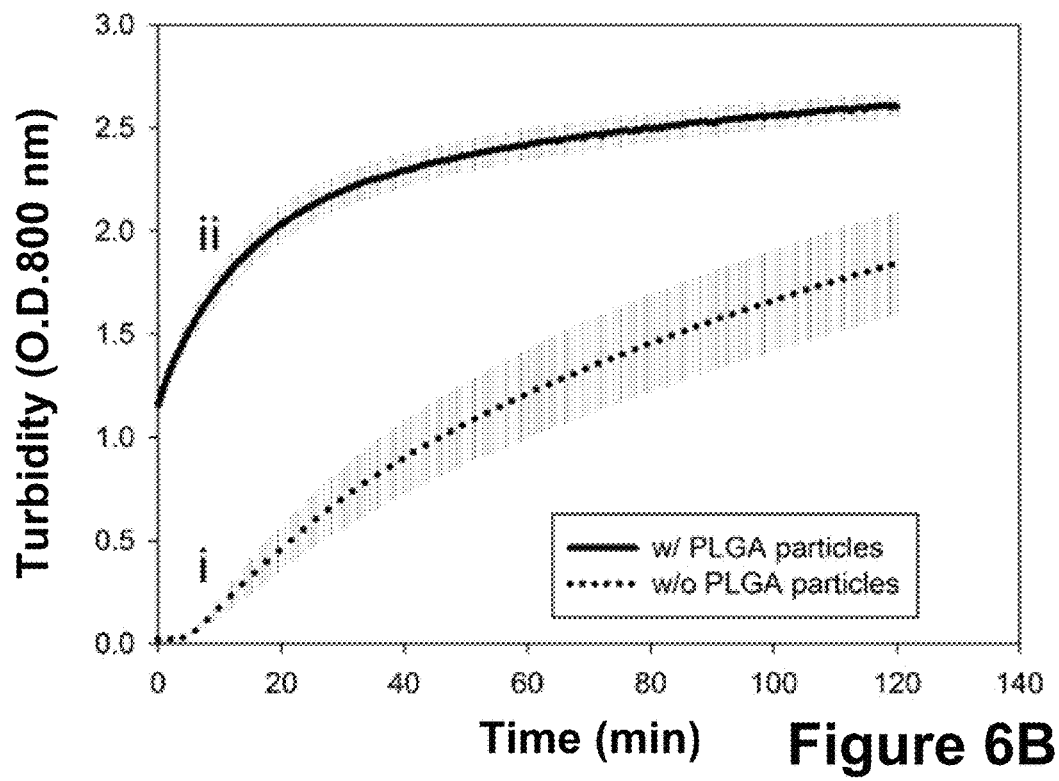
FIG. 6B shows the kinetic turbidity changes over 2 hours for SNO-silica formation and deposition with and without PLGA NPs.
Figure 6C:
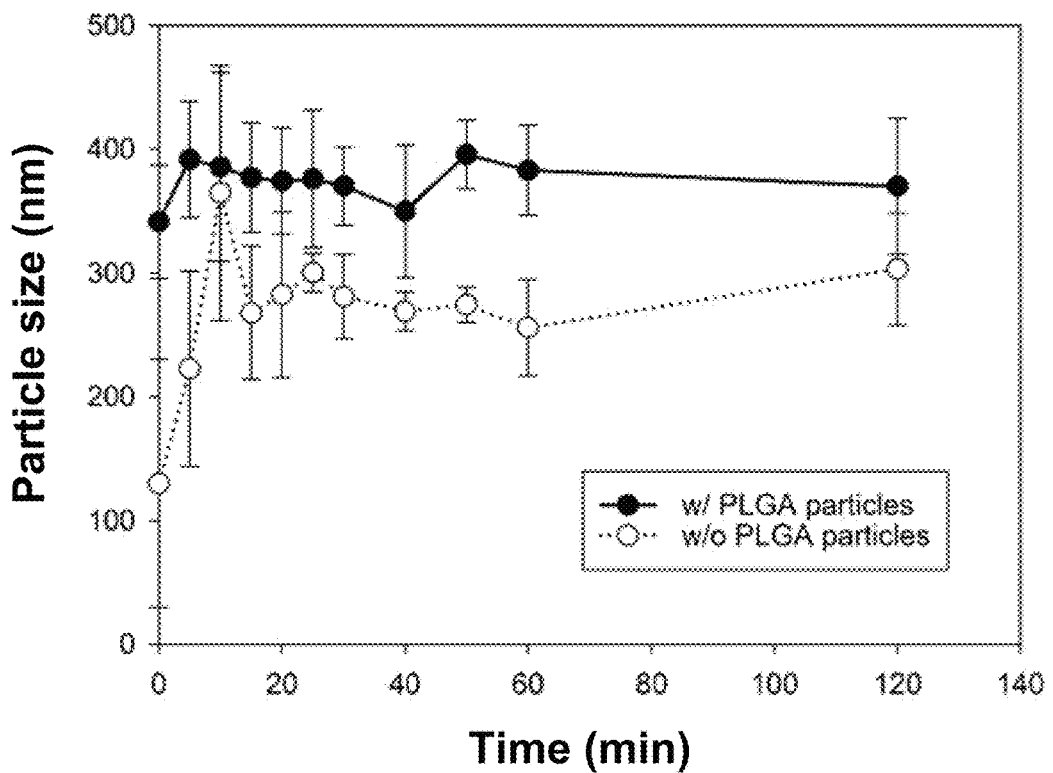
FIG. 6C shows the change of hydrodynamic sizes over time for SNO-silica formation and deposition with and without PLGA NPs.

To understand the underlying mechanism, the inventors demonstrate the important role of acid-mediated surface deposition of SNO silica species. FIG. 5 shows the pictures of the reaction mixture after the solvent evaporation step and those of final dispersions. When the reaction mixture containing PLGA NPs (white) and SNO silica species (red) was left standing without further adding HCl, the final collected particle dispersion (after centrifuging and redispersing in water) revealed the whitish color of PLGA NPs. This suggests that SNO silica species has not been deposited on PLGA NPs. However, when HCl was added to the reaction mixture, the final collected particles were reddish, suggesting that SNO silica has been attached to PLGA NPs. To directly observe the effect of acid on silica precipitation, the solvent-evaporated reaction mixture was centrifuged to remove PLGA NPs from solution. The transparent reddish solution was then subjected to acid addition. After adding HCl, the solution became increasingly opaque, as indicated by the corresponding image taken at 20 min (FIG. 6A, image i) and the kinetic turbidity trace over time (FIG. 6B, trace i). Notably, very fast particle formation upon acid addition can be detected by DLS measurements; the size (in the absence of PLGA NPs) reaches about 250-300 nm at 10 min and remains the same over time (FIG. 6C). Since PLGA NPs have been removed, the detected particles in the control solution represent nanoaggregates of SNO silica species. In contrast, in the presence of PLGA NPs, the solution is initially turbid and became much more turbid over time after acid addition (image and trace ii). Interestingly, the initial mean particle size for PLGA NPs was about 350 nm and the addition of HCl resulted in only a slight size increase (<50 nm, FIG. 6C). The result suggests that Janus particles were formed not through direct fusion of two particle entities, i.e. existing PLGA NPs and newly formed silica NPs, given that a direct unforced sticking of the two large particles (each about the size of 300 nm) would produce even larger particles.

Figure 7B:
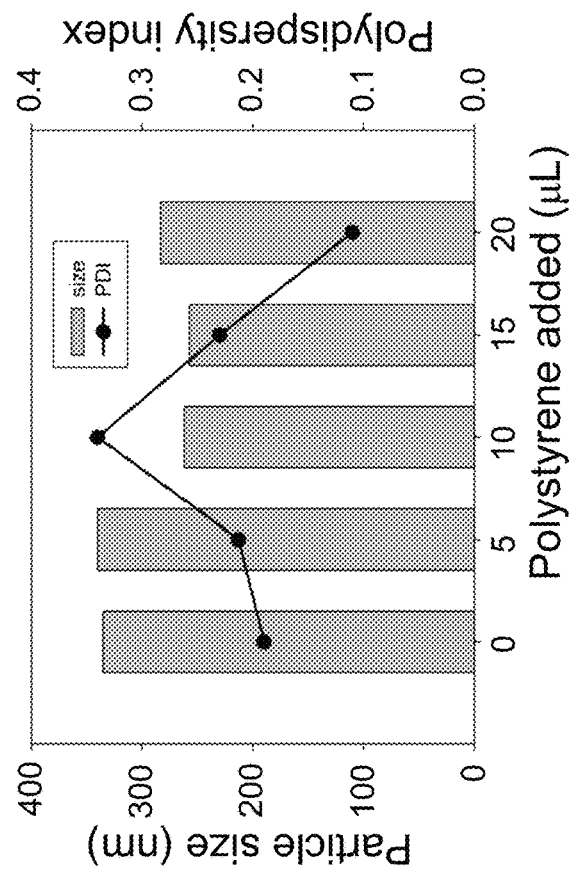
FIG. 7B shows hydrodynamic sizes and polydispersity (pdi) after 60 min of reaction for the SNO-silica deposition in the presence of polystyrene (PS) NPs.
Figure 7A:
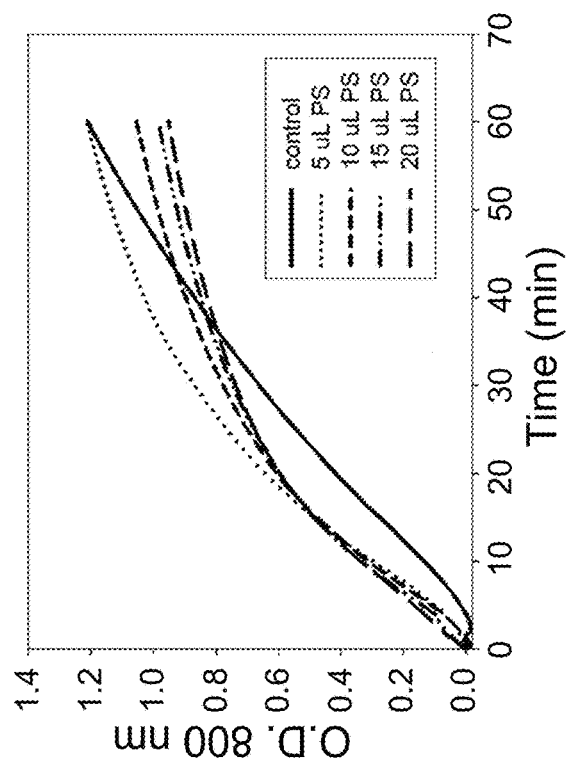
FIG. 7A shows kinetic turbidity traces without and with various amount of added PS NPs for the SNO-silica deposition in the presence of polystyrene (PS) NPs.
Figure 7C:
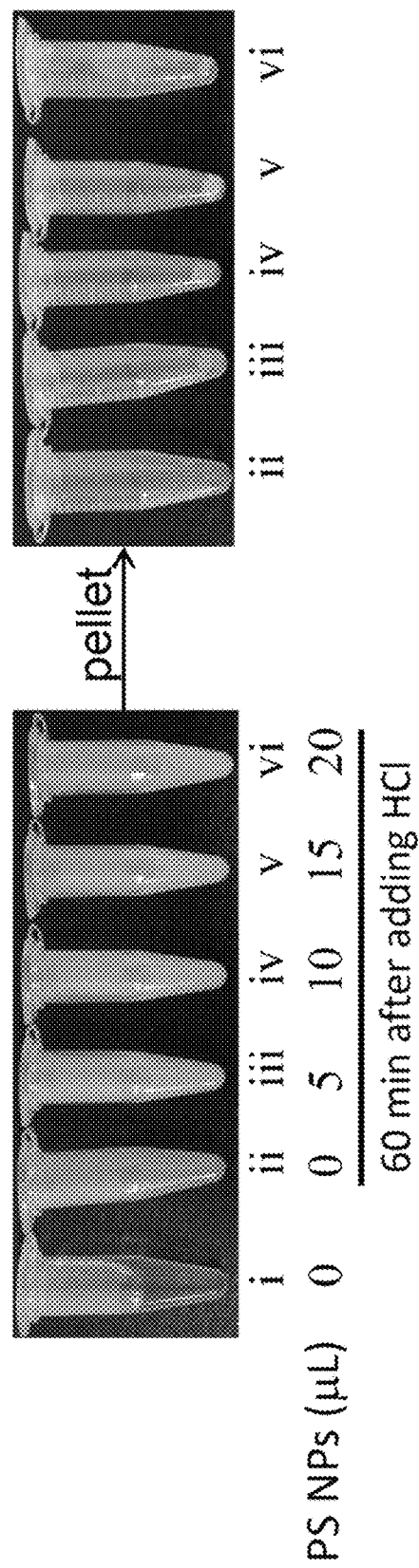
FIG. 7C shows the photo images of the reaction mixture for the SNO-silica deposition in the presence of polystyrene (PS) NPs before and after centrifugation with (i) 0 μL of PS NPs, (ii) 0 μL of PS NPs and reacting 60 minutes after adding HCl, (iii) 5 μL of PS NPs and reacting 60 minutes after adding HCl, (iv) 10 μL of PS NPs and reacting 60 minutes after adding HCl, (v) 15 μL of PS NPs and reacting 60 minutes after adding HCl, (vi) 20 μL of PS NPs and reacting 60 minutes after adding HCl.

To extend the scope of this study and also provide further evidence to support the above premise, an additional experiment was conducted in which the effect of acid-induced silica precipitation was investigated by replacing PLGA NPs with polystyrene nanoparticles (PS NPs), and replenishing particle-free "SNO silica soup" with PS NPs. Generally, the results shown in FIG. 7 reveal that SNO silica species can be deposited on PS NPs with the help of added HCl. Specifically, first, the kinetic turbidity profile was markedly affected by the presence of PS NPs (FIG. 7A). Increasing the amount of PS NPs added would initially facilitate the turbidity increase so that the lag phase (about 5 min) observed in the control solution became less noticeable. However, turbidity leveled off more quickly with lower final turbidity at higher NP concentrations. The turbidity data correspond to the second observation that smaller and more homogeneous particles were determined at high NP concentrations (FIG. 7B). It is important to note that the final particle size after silica deposition is about the size of the original PS NPs, if sufficient NPs were added. In contrast, without PS NPs, the silica particles formed from the control solution were even larger. Again, the data possibly reject the direct fusion hypothesis in which two large particles joined to form Janus particles. FIG. 7C confirms the deposition of SNO silica on PS NPs, as the original PS NPs are white.

Figure 8A:
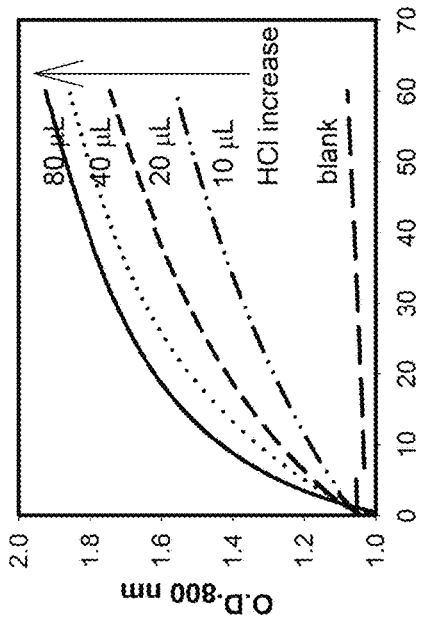
FIG. 8A shows the effect of HCl on silica deposition: the absorbance (330 nm) of the supernatant during after adding 5 M HCl (increasing from 0 (blank), 10, 20, 40, and 80 μL).
Figure 8B:
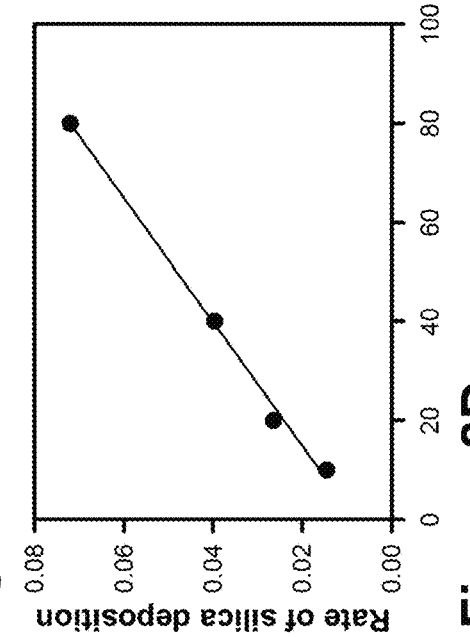
FIG. 8B shows the effect of the turbidity increase over time after adding HCl (the direction of the arrow indicates the increase of HCl).
Figure 8C:
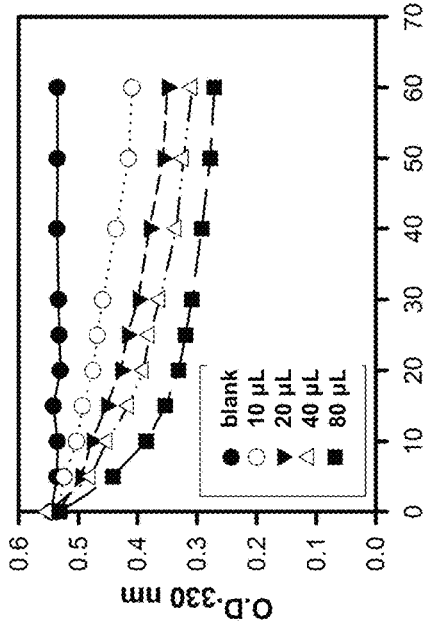
FIG. 8C shows the effect of the correlation between SNO entrapment and silica deposition.
Figure 8D:
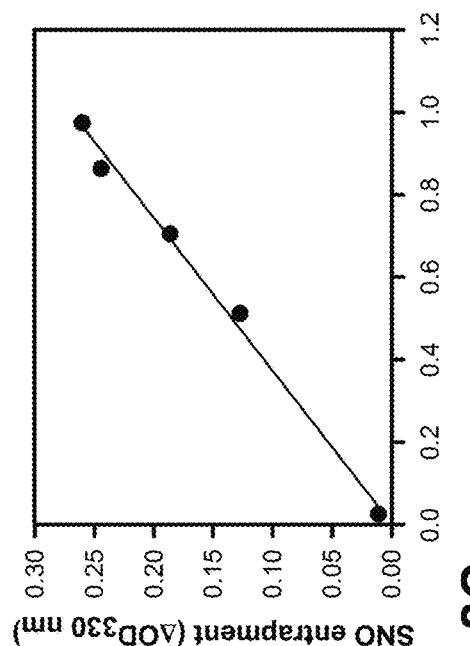
FIG. 8D shows the effect of the dependence of silica deposition on the amount of HCl added.

To further characterize acid-mediated deposition of SNO silica species, the inventors measured the decay kinetics of SNO species in the bulk solution upon adding various amounts of HCl and compared the result with the kinetic turbidity data. The SNO level was measured spectrophotometrically at 330 nm after separating PLGA NPs from the bulk solution by centrifugation. It can be seen from FIG. 8A that the SNO level in the bulk solution remained unchanged over time when acid was not added; however, the addition of HCl triggered the decay of SNO levels and the extent of decay seemed to correlate with the amount of HCl added: i.e. faster SNO decay with higher HCl concentrations. The continuing decrease of SNO levels can be attributed to the entrapment of SNO silica species onto PLGA NPs, because the particle pellets become reddish over time. The kinetics of turbidity changes were simultaneously measured and the data presented in FIG. 8B clearly reveal the crucial role of HCl addition in the system. Specifically, the system responded immediately upon HCl addition by increasing turbidity over time, and the higher amount of HCl added, the faster the turbidity was increased. The increase in turbidity suggests that silica precipitation/deposition has been initiated. Remarkably, when the extent of SNO entrapment (decrease in $OD_{330\ nm}$ at 60 min) was plotted against that of silica deposition (increase in $OD_{800\ nm}$ at 60 min), a good linear relationship was obtained (FIG. 8C). Furthermore, the rate of silica deposition measured as the rate of turbidity increase correlated well with the amount of HCl added (FIG. 8D). Overall, the results indicate that acid-addition in the final step mediates simultaneous formation and deposition of SNO silica nanoparticles.

Figure 9A:
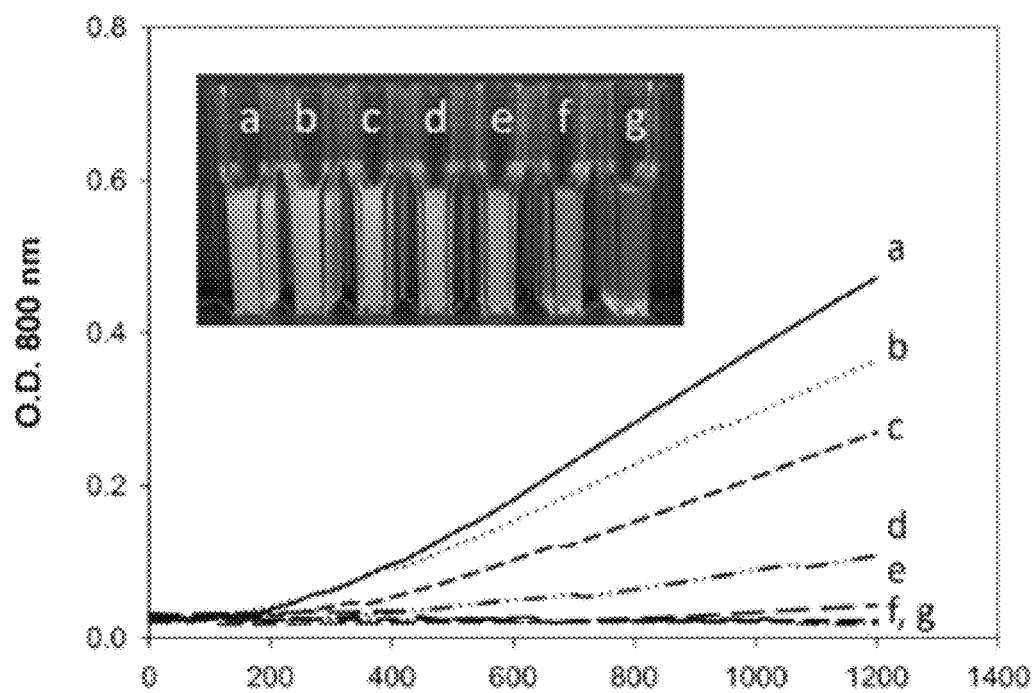
FIG. 9A shows the effect of diluting the SNO-silica supernatant on silica deposition: kinetic turbidity traces for different dilutions (100% (a), 95% (b), 90% (c), 80% (d), 70% (e), 60% (f), 50% (g) of the original supernatant solution).
Figure 9B:
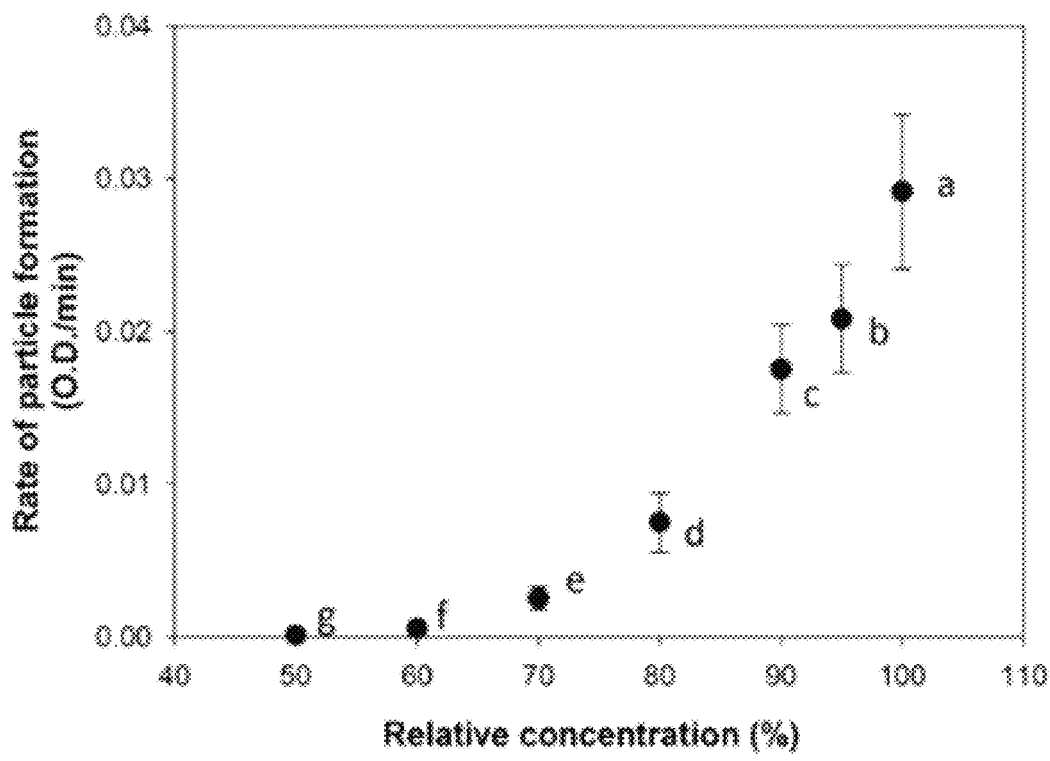
FIG. 9B shows the effect of diluting the SNO-silica supernatant on silica deposition: rate of particle formation as a function of relative concentration.

As indicated above, the particle-free, blank "SNO silica soup" was initially transparent and it became increasingly turbid when HCl was added to the solution. It is however noted that there is a lag time, followed by an acceleration phase, in the kinetic turbidity trace for the blank solution. Apparently, in the absence of PLGA NPs, the process of silica deposition is kinetically controlled. The inventors speculate that the occurrence of an initiation phase may be attributed to acid-mediated polymerization of SNO-functionalized MPMDMS, which produces hydrophobic polycondensed species. Thus, during the lag period, hydrophobic species accumulates, and after reaching a critical concentration, it undergoes a homogeneous nucleation and phase separation process. Indeed, FIG. 9 shows that such a process is highly dependent on the initial SNO silane concentrations. By serially diluting the SNO silica solution and then adding HCl to each diluted solution, the inventors found that the buildup of the solution turbidity was significantly quenched with increasing dilutions (FIG. 9A). By plotting the rate of particle formation (i.e. rate of turbidity change) against relative silane concentrations, the results reveal a critical phenomenon in which significant particle formation occurred only at above a critical silane concentration.

Kinetics of Nitric Oxide Release

Figure 10:
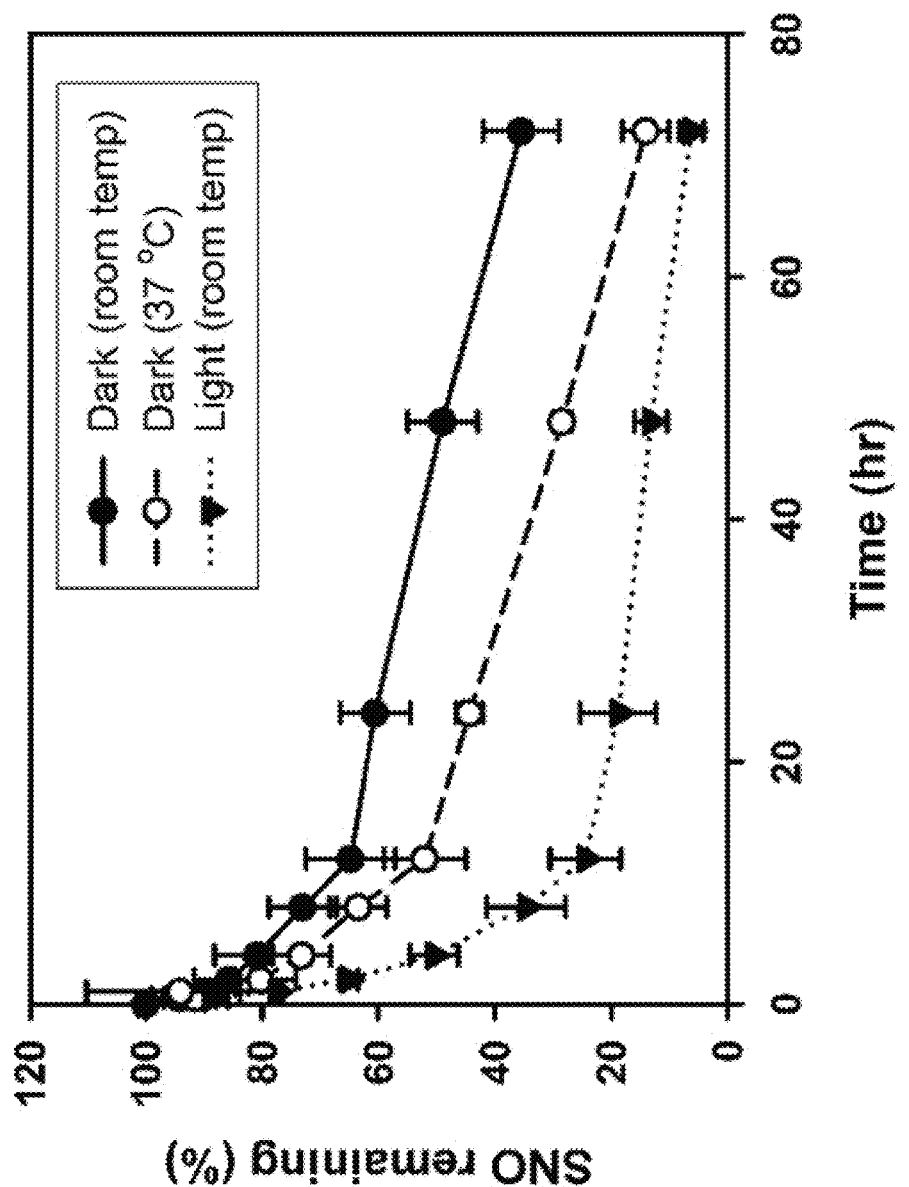
FIG. 10 shows that SNO remaining as a function of time during the NO release study.

SNO linkage is subjected to thermal and light mediated degradation, leading to the release of nitric oxide. To characterize the NO-release property of as-prepared Janus particles, the inventors determined the remaining SNO level in Janus particles over time in aqueous dispersions with or without light exposure. FIG. 10 shows that SNO decomposed much more rapidly when the sample was exposed to light than at dark. Besides that, higher decomposition rate can be observed at 37° C. than at room temperature (24° C.). Thus, the data further demonstrate that SNO has been successfully attached and loaded in the PLGA-Si Janus NPs.

Janus PLGA-Silica Nanoparticles for Delivering Nitric Oxide and Temoxolomide (TMZ)

Figure 12:
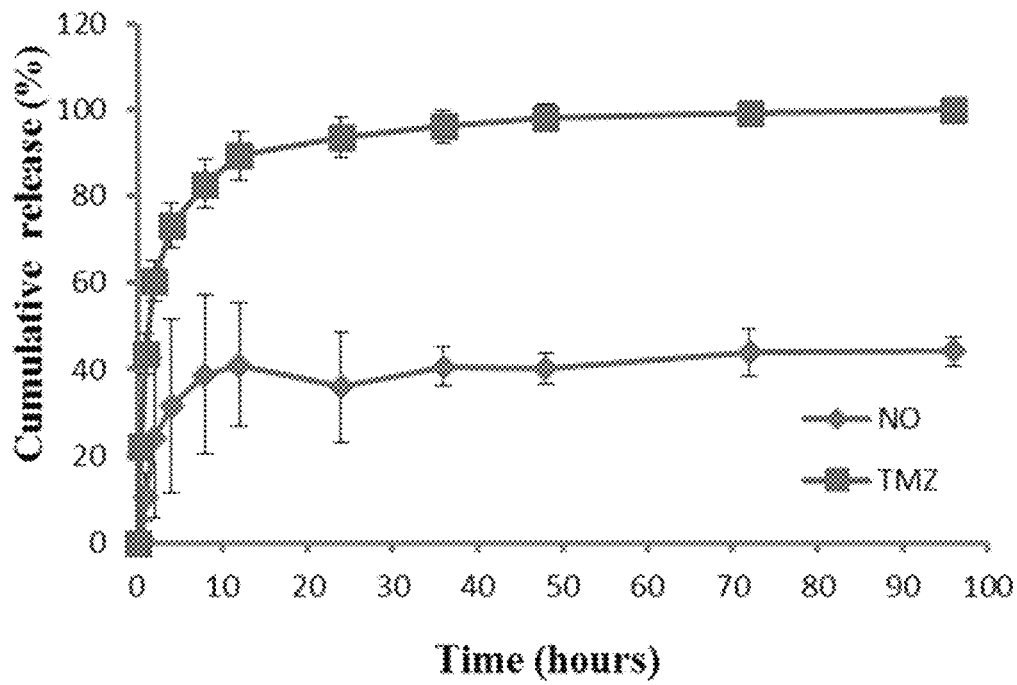
FIG. 12 shows in vitro drug releasing curves of the Janus PLGA-silica nanoparticles in PBS, pH 7.4 (n=3).

FIG. 11 depicts a procedure for synthesis of S-nitroso (SNO) carrying TMZ-loaded PLGA-silica Janus nanoparticles. Several key preparation parameters were identified and studied: reagent concentration, solvent, particle sizes, and reaction time. The results are shown in Table 1, indicating the particle size is about 300 nm and the loading rete of the chemotherapy drug TMZ is about 50%. Furthermore, a primary releasing test shows that the Janus PLGA-silica nanoparticles of the present invention release TMZ and nitric oxide in PBS (FIG. 12).

TABLE 1

Formulation and TMZ loading rate of the Janus PLGA-silica nanoparticles

| Formulation | TMZ OD (stock) | TMZ OD (sample) | Volume | EE % |
| --- | --- | --- | --- | --- |
| 5 mg TMZ/20 mg PLGA: 1% PVA (2/5, v/v) 20A, 2 min | 1.339 | 0.42 | 4.5 | 37.9 |
| 5 mg TMZ/20 mg PLGA: 1% PVA (2/5, v/v) 30A, 2 min | 1.339 | 0.423 | 4 | 44.4 |
| 5 mg TMZ/20 mg PLGA: 1% PVA (2/5, v/v) 40A, 2 min | 1.339 | 0.408 | 4.2 | 43.6 |
| 5 mg TMZ/20 mg PLGA: 1% PVA (2/5, v/v) 50A, 2 min | 1.339 | 0.392 | 3.8 | 51.1 |

Figure 13:
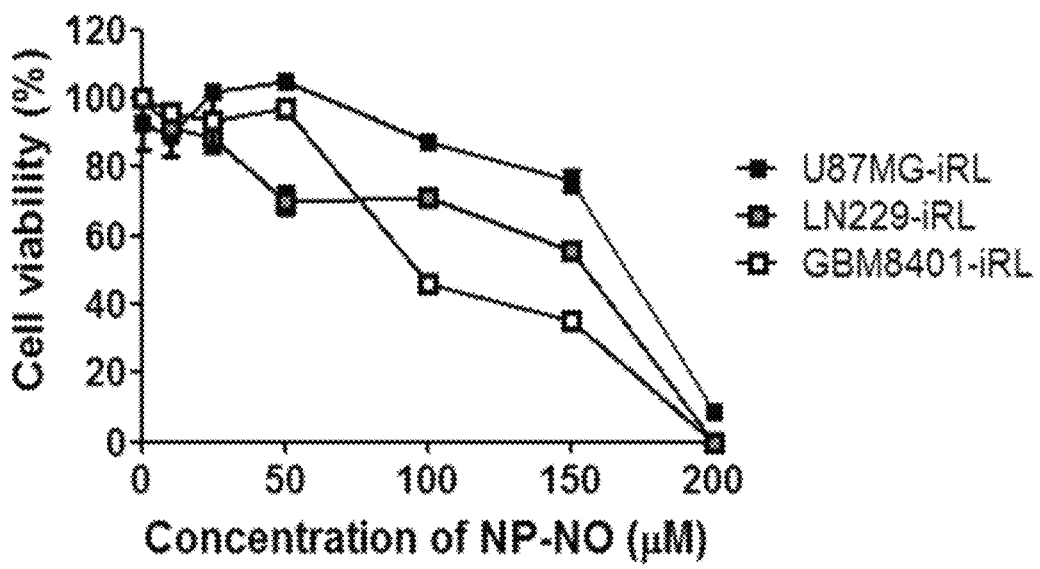
FIG. 13 shows cytotoxicity of different concentrations of Janus PLGA-silica nanoparticles to glioblastoma cell lines U87, LN229, and GBM8401, respectively.

Cytotoxicity of Nitric Oxide-Loaded Janus PLGA-Silica Nanoparticles to Cancer Cell Lines Glioblastoma cell lines U87, LN229, and GBM8401 were treated with several concentrations of the Janus PLGA-silica nanoparticles of the present invention to analyze the cytotoxicity of the nanoparticles. Viabilities of these cell lines were measured by the MTS assay. The results show dose-dependent inhibitions of all the cancer cell lines (FIG. 13), indicating that the Janus PLGA-silica nanoparticles of the present invention inhibit proliferation of all the three glioblastoma cell lines.

Figure 14:
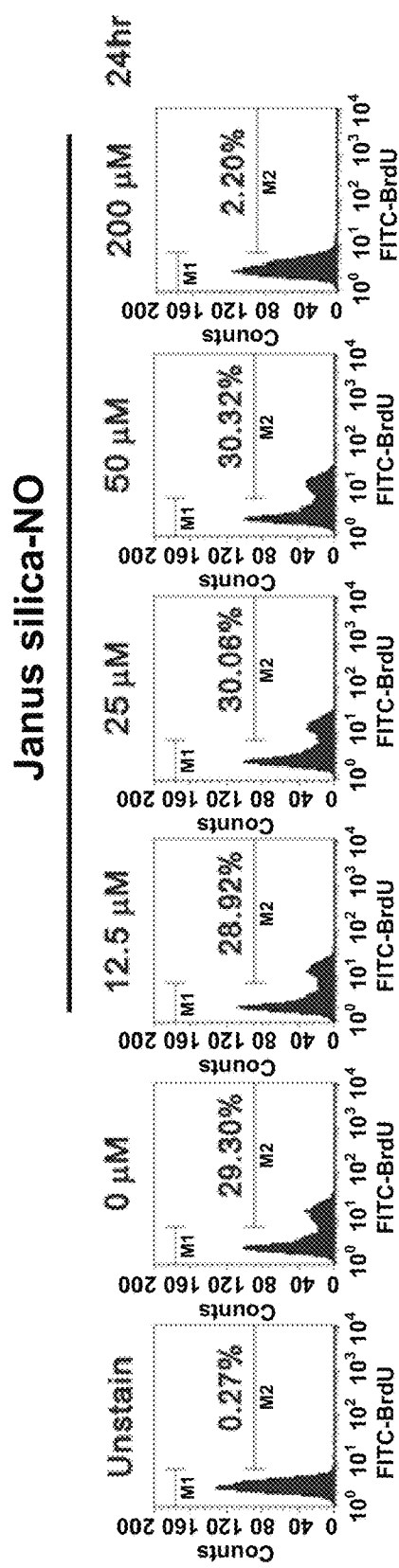
FIG. 14 shows proliferation inhibitory of 200 μM of Janus PLGA-silica nanoparticles to glioblastoma cell line GBM8401.

Furthermore, glioblastoma cell line GBM8401 was treated with 200 μM of Janus PLGA-silica nanoparticles of the present invention for 24 hours. After that, DNA of the cancer cells was labeled with 5-bromo-2'-deoxyuridine (BrdU), and cell proliferation was analyzed by flow cytometry. FIG. 14 shows that 200 μM of the Janus PLGA-silica nanoparticles of the present invention significantly inhibit cell proliferation of glioblastoma cell line GBM8401.

Figure 15A:
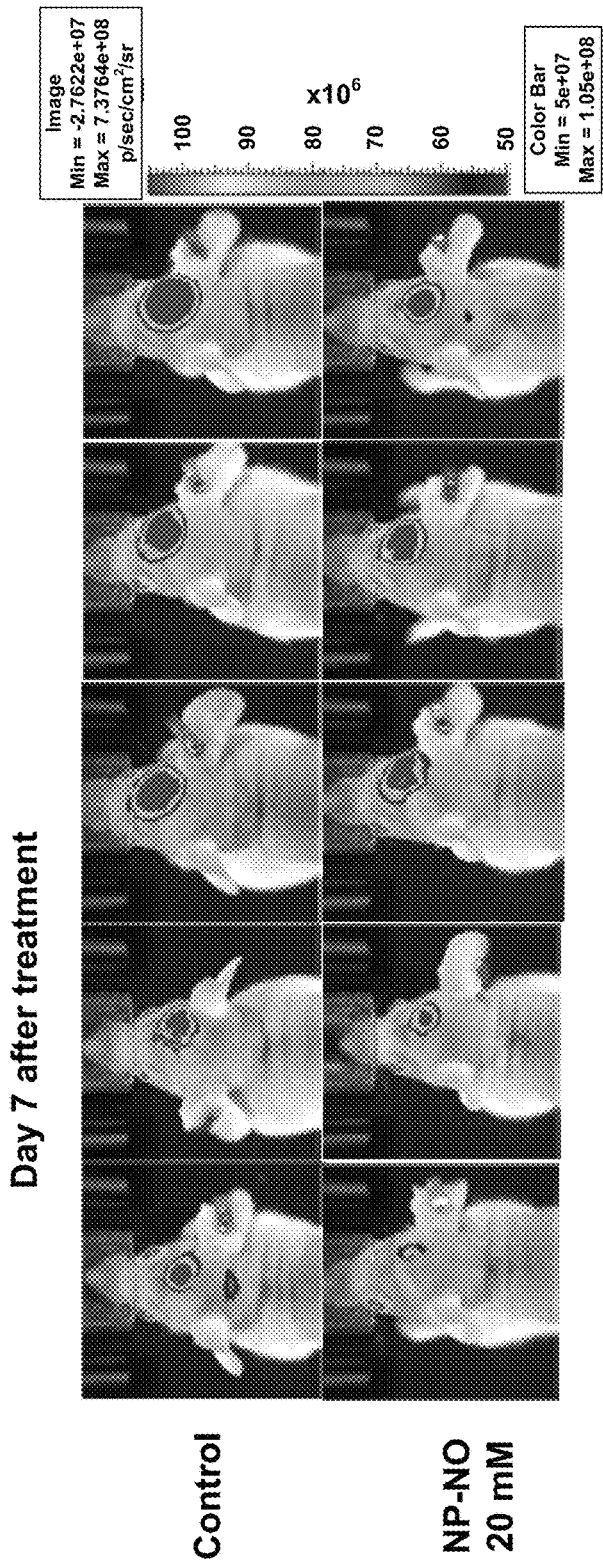
FIG. 15A shows in vivo inhibition of brain tumor growth by the Janus PLGA-silica nanoparticles, where the tumor images labeled with bioluminescence.
Figure 15B:
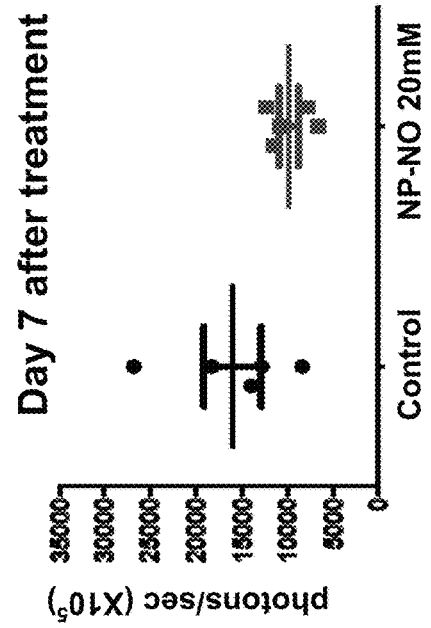
FIG. 15B shows the tumor sizes quantified by the bioluminescent signals for in vivo inhibition of brain tumor growth by the Janus PLGA-silica nanoparticles. The results were expressed as the mean±standard deviation (SD) (n=5).

In Vivo Inhibition of Brain Tumor Growth by the Nitric Oxide-Loaded Janus PLGA-Silica Nanoparticles Nude mice bearing brain tumor xenografts were used as the animal model to analyze anticancer effect of the Janus PLGA-silica nanoparticles of the present invention. A human brain malignant glioma cell line, GBM8401-iRL was transplanted in the brains of 6-week-old nude mice. Five days later, the Janus PLGA-silica nanoparticles of the present invention were implanted around the tumors. Seven (7) days after the treatment, sizes of the tumors in the animal model were measured by the In Vivo Imaging System (IVIS). The results are shown in FIGS. 15A and 15B, indicating that compared with the control group, treatment of the Janus PLGA-silica nanoparticles of the present invention significantly inhibits tumor growth in mice brains (n=5).

Figure 16A:
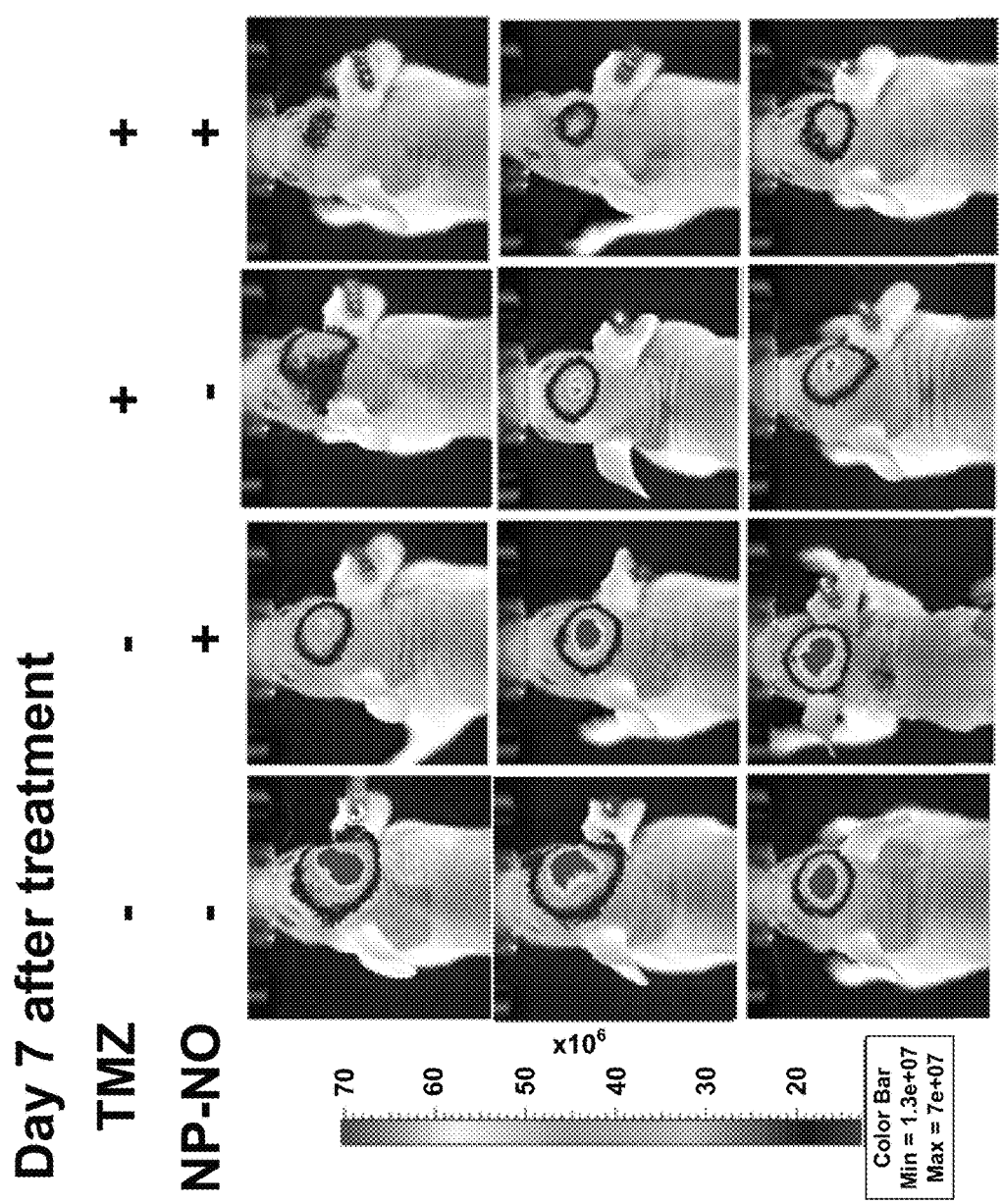
FIG. 16A shows in vivo inhibition of brain tumor growth by combination of the Janus PLGA-silica nanoparticles and TMZ, where the tumor images labeled with bioluminescence.
Figure 16B:
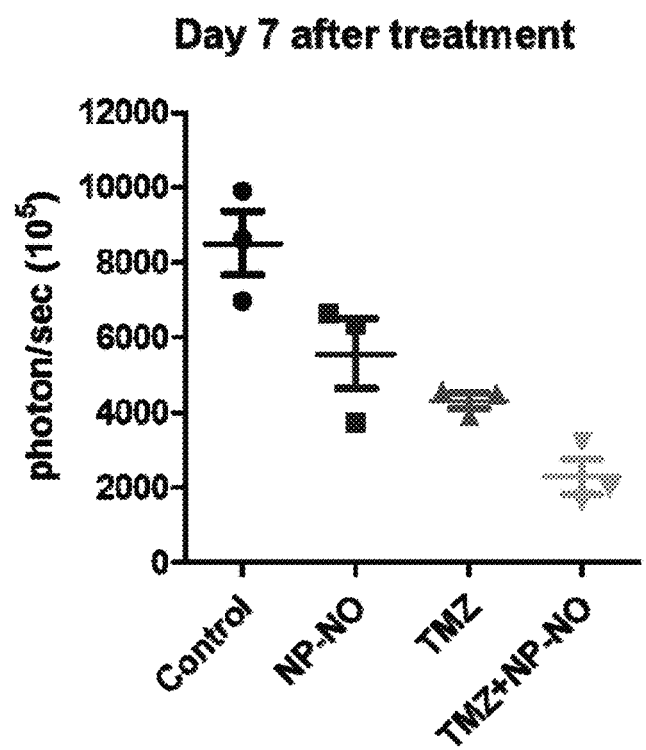
FIG. 16B shows the tumor sizes quantified by the bioluminescent signals for in vivo inhibition of brain tumor growth by combination of the Janus PLGA-silica nanoparticles and TMZ. The results were expressed as the mean±standard deviation (SD) (n=5).
Figure 16C:
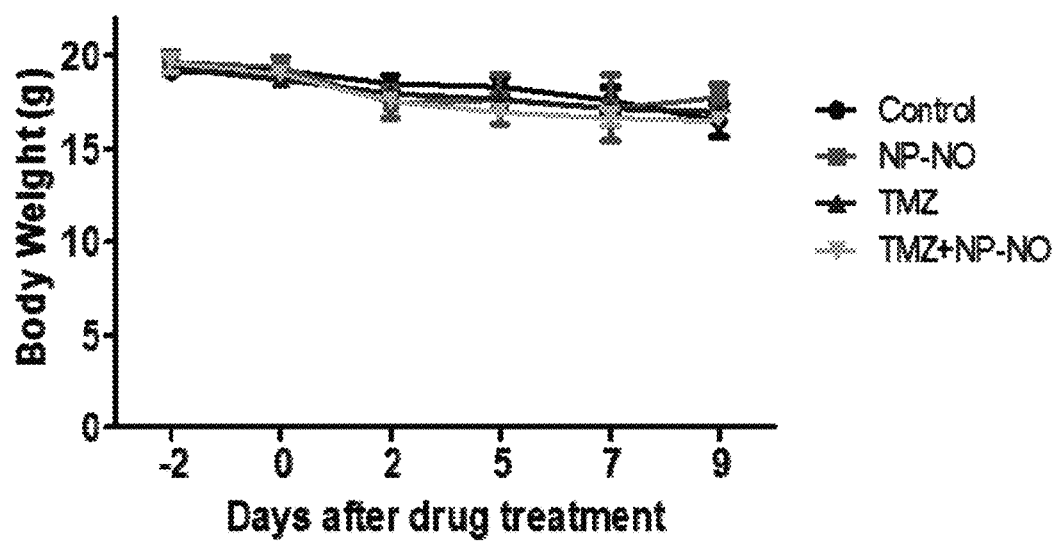
FIG. 16C shows body weights of the mice for in vivo inhibition of brain tumor growth by combination of the Janus PLGA-silica nanoparticles and TMZ, where no significant difference among the body weights of the mice in treatment groups and in the control group.

In Vivo Inhibition of Brain Tumor Growth by Combination of the Nitric Oxide-Loaded Janus PLGA-Silica Nanoparticles and TMZ Nude mice bearing brain tumor xenografts were also used as the animal model to analyze anticancer effect of the combination of the Janus PLGA-silica nanoparticles of the present invention and a chemotherapy drug TMZ. A human brain malignant glioma cell line, GBM8401-iRL was transplanted in the brains of 6-week-old nude mice. Five days later, the Janus PLGA-silica nanoparticles of the present invention were implanted around the tumors, followed by intraperitoneal injection of TMZ for 3 days. Sizes of the tumors in the animal model were traced with the In Vivo Imaging System (IVIS). The results are shown in FIGS. 16A to 16C, indicating that treatment of the combination of the Janus PLGA-silica nanoparticles of the present invention and TMZ inhibits tumor growth in mice brains more significantly than treatment of the Janus PLGA-silica nanoparticles of the present invention alone and treatment of TMZ alone (FIGS. 16A and 16B). In addition, drug toxicity was analyzed by measuring the body weights of the animal model. The results show that no significant difference among the body weights of the mice in treatment groups and in the control group (FIG. 16C), suggesting that the Janus PLGA-silica nanoparticles of the present invention possess no acute toxicity to the animal.

Figure 17A:
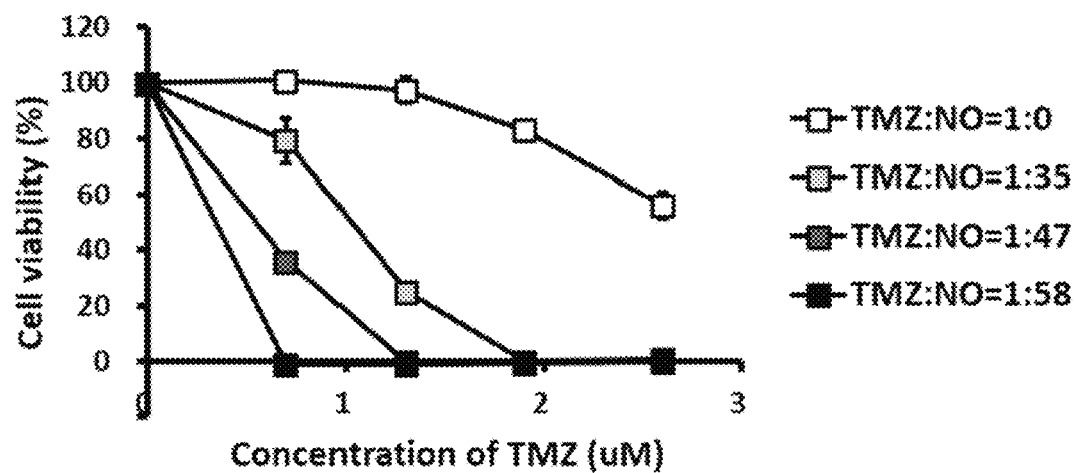
FIG. 17A shows cytotoxicity of Janus PLGA-silica nanoparticles loaded both TMZ and various concentrations of nitric oxide to glioblastoma cell lines LN229.
Figure 17B:
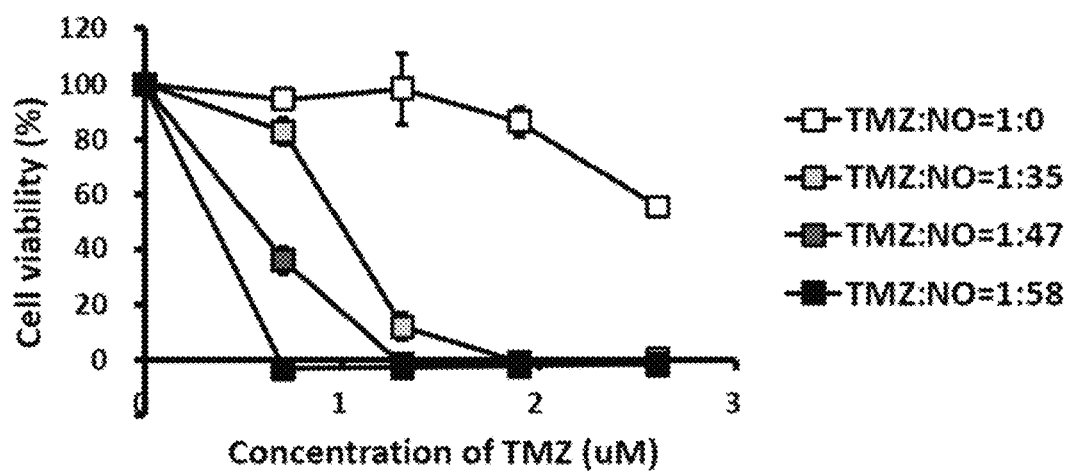
FIG. 17B shows cytotoxicity of Janus PLGA-silica nanoparticles loaded both TMZ and various concentrations of nitric oxide to GBM8401.

Cytotoxicity of Nitric Oxide and TMZ-Loaded Janus PLGA-Silica Nanoparticles to Cancer Cell Lines Glioblastoma cell lines, LN229 and GBM8401, were treated with several concentrations of the Janus PLGA-silica nanoparticles of the present invention to analyze the cytotoxicity of the nanoparticles. Viabilities of these cell lines were measured by the MTS assay. The results show TMZ-loaded Janus PLGA-silica nanoparticles (TMZ:NO=1:0) dose-dependent inhibitions of all the cancer cell lines. Janus PLGA-silica nanoparticles loaded both TMZ and various concentrations of nitric oxide synergistically reduced cell viability (FIG. 17). This result indicates that the Janus PLGA-silica nanoparticles of the present invention can reduced cell viability of both of the glioblastoma cell lines.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A complex particle for delivering nitric oxide, comprising a poly(Lactide-co-Glycolide) (PLGA) nanoparticle and a S-nitroso-silica species depositing on the PLGA nanoparticle wherein the complex particle is made by steps of: injecting an organic phase to a water phase to obtain a mixture, the organic phase containing (3-Mercaptopropyl) methyldimethoxysilane (MPMDMS) and PLGA in acetone, and the water phase containing poly(vinyl alcohol) (PVA), sodium nitrite, and hydrochloric acid (HCl) in water; removing acetone from the mixture; and adding a second HCl to the mixture to initiate silica disposition.

2. The complex particle of claim 1, wherein the PLGA has a lactide/glytide ratio, and the lactide/glycolide ratio is 50/50 to 85/15.

3. The complex particle of claim 1, wherein the MPMDMS has a concentration ranging from 20 to 80 mM.

4. The complex particle of claim 1, further comprising a drug loaded on the PLGA nanoparticle.

5. The complex particle of claim 4, wherein the complex particle is made by steps of:
   injecting an organic phase to a water phase to obtain a mixture, the organic phase containing MPMDMS, PLGA, and a drug in acetone, and the water phase containing PVA, sodium nitrite, and HCl in water;
   removing acetone from the mixture; and
   adding a second HCl to the mixture to initiate silica disposition.

6. The complex particle of claim 5, wherein the PLGA has a lactide/glycolide ratio, and the lactide/glycolide ratio is 50/50 to 85/15.

7. The complex particle of claim 5, wherein the MPMDMS has a concentration ranging from 20 to 80 mM.

8. A method of producing a complex particle for delivering nitric oxide, comprising steps of:
   injecting an organic phase to a water phase to obtain a mixture, the organic phase containing (3-Mercaptopropyl)methyldimethoxysilane (MPMDMS) and Poly (Lactide-co-Glycolide) (PLGA) in acetone, and the water phase containing poly(vinyl alcohol) (PVA), sodium nitrite, and hydrochloric acid (HCl) in water;
   removing acetone from the mixture; and
   adding a second HCl to the mixture to initiate silica disposition.

9. The method of claim 8, wherein the PLGA has a lactide/glycolide ratio, and the lactide/glycolide ratio is 50/50 to 85/15.

10. The method of claim 8, wherein the MPMDMS has a concentration ranging from 20 to 80 mM.

11. The method of claim 8, wherein the organic phase further contains a drug in acetone.

12. The method of claim 11, wherein the PLGA has a lactide/glycolide ratio, and the lactide/glycolide ratio is 50/50 to 85/15.

13. The method of claim 11, wherein the MPMDMS has a concentration ranging from 20 to 80 mM.

14. A method for inhibiting tumor growth, comprising administering an effective amount of the complex particle for delivering nitric oxide of claim 1 to a subject in need.

15. The method of claim 14, wherein the complex particle is made by steps of:
   injecting an organic phase to a water phase to obtain a mixture, the organic phase containing MPMDMS and PLGA in acetone, and the water phase containing poly(vinyl alcohol) (PVA), sodium nitrite, and hydrochloric acid (HCl) in water;
   removing acetone from the mixture; and
   adding a second HCl to the mixture to initiate silica disposition.

16. The method of claim 15, wherein the PLGA has a lactide/glycolide ratio, the lactide/glycolide ratio is 50/50 to 85/15, and the MPMDMS has a concentration ranging from 20 to 80 mM.

17. The method of claim 14, wherein the complex particle further comprises an anti-cancer drug loaded on the PLGA nanoparticle.

18. The method of claim 17, wherein the complex particle is made by steps of:
   injecting an organic phase to a water phase to obtain a mixture, the organic phase containing MPMDMS, PLGA, and the anti-cancer drug in acetone, and the water phase containing PVA, sodium nitrite, and HCl in water;
   removing acetone from the mixture; and
   adding a second HCl to the mixture to initiate silica disposition.

19. The method of claim 18, wherein the PLGA has a lactide/glycolide ratio, the lactide/glycolide ratio is 50/50 to 85/15, and the MPMDMS has a concentration ranging from 20 to 80 mM.

* * * * *